United States Patent [19]
Foster et al.

[11] Patent Number: 5,880,163
[45] Date of Patent: Mar. 9, 1999

[54] OIL COMPOSITION OF DIHYDROPOLYPRENOLS

[75] Inventors: Todd P. Foster, Kalamazoo; Karen Barsuhn, Plainwell, both of Mich.

[73] Assignee: Pharmacia & Upjohn Company, Kalamazoo, Mich.

[21] Appl. No.: 998,012

[22] Filed: Dec. 3, 1997

Related U.S. Application Data

[60] Provisional application No. 60/033,182, Dec. 12, 1996.
[51] Int. Cl.$^6$ .................................................. A61K 31/045
[52] U.S. Cl. .............................................................. 514/739
[58] Field of Search .............................................. 514/739

[56] References Cited

U.S. PATENT DOCUMENTS

| | | | |
|---|---|---|---|
| 4,624,966 | 11/1986 | Yamamoto et al. | 514/724 |
| 4,839,389 | 6/1989 | Koyama et al. | 514/724 |
| 5,139,740 | 8/1992 | Uesugi et al. | 424/451 |
| 5,280,048 | 1/1994 | Yamamoto et al. | 514/739 |

FOREIGN PATENT DOCUMENTS

| | | | |
|---|---|---|---|
| 0 041 235 | 12/1981 | European Pat. Off. | C07C 69/52 |
| 0 239 7729 | 10/1987 | European Pat. Off. | C07C 69/52 |
| 0 350 801 | 1/1990 | European Pat. Off. | A61K 31/045 |
| 0 538 572 | 2/1994 | European Pat. Off. | C07C 33/02 |
| 29 47 624 A | 6/1980 | Germany | C07C 33/02 |

OTHER PUBLICATIONS

H. Nagahata, G. J. Kociba, H. Noda, M. Koiwa and M. Kimura, "Effects of Dihydroheptaprenol on the Neutrophil Function of Postpartum Dairy Cows", *Veterinary Immunology and Immunopatholgy*, 29, pp. 163–169 (1991).

O. Yoneyama, S. Osame, S. Ichijo, M. Kimura, S. Araki, M. Suzuki and E. Imamura, "Effects of Dihydroheptaprenol on Neutrophil Functions in Calves", *British Veterinary Journal*, 145, pp. 531–537 (1989).

O. Yoneyama, S. Osame, M. Kimura, S. Araki and S. Ichijo, "Enhancement of Neutrophil Function by Dihydroheptaprenol in Adult Cows", *Japan Journal of Veterinary Science*, 51(6), pp. 1283–1286 (1989).

T. Watari, R. Goitsuka, H. Koyama, T. Sako, T. Uchino, S. Araki, A. Hasegawa and S. Motoyoshi, "Effect of Dihydroheptaprenol on Nitroblue Tetrazolium Reduction by Swine Alveolar Macrophages", *Japan Journal of Veterinary Science*, 51(3), pp. 630–631 (1989).

S. Araki, M. Suzuki, K. Ogura, M. Kumura, E. Imamura, C. Kuniyasu, K. Kagaya and Y. Fukazawa, "Enhancement of Phagocytosis and Bactericidal Activity of Neutrophils in Miniature Pigs by Dihydroheptaprenol, A Synthetic Polyprenol Derivative", *Microbiology, Immunol.*, 33(10), pp. 877–882 (1989).

S. Araki, K. Kagaya, K. Kitoh, M. Kimura and Y. Fukazawa, "Enhancement of Resistance to *Escherichia Coli* Infection in Mice by Dihydroheptaprenol, a Synthetic Polyprenol Derivative", *Infection and Immunity*, 55(9), pp. 2164–2170 (1987).

M. Kimura, S. Araki, T. Nakai and K. Kume, "Protective Effect of Dihydroheptaprenol in Combination with Vaccine to Experimental Actinobacillus Pleuropneumoniae Injection in Guinea Pigs and Pigs", *Japan Journal of Veterinary Science*, 55(4), pp. 627–630 (1993).

E. J. Robb, D. D. Kratzer, C. H.–Ho, and K. J. Dame, "Dose Characterization and Dosage Regime Evaluation of Dihydroheptaprenol in Induced Bovine Pneumonic Pasteurellosis", *Journal of Animal Science*, 71 (Suppl. 1), p. 203 (1993).

*Primary Examiner*—Raymond Henley, III
*Attorney, Agent, or Firm*—Lucy X. Yang

[57] ABSTRACT

The present invention provides an oil composition for parenteral administration comprising a dihydropolyprenol of formula I and a pharmaceutically acceptable oil

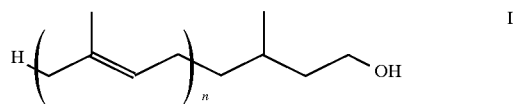

wherein n is an integer of 5 to 7.

10 Claims, No Drawings

OIL COMPOSITION OF DIHYDROPOLYPRENOLS

CROSS-REFERENCE TO RELATED APPLICATION

This application claims the benefit of the following provisional application: U.S. Ser. No. 60/033,182, filed Dec. 12, 1996, under 35 USC 119(e)(i).

FILED OF THE INVENTION

The present invention relates to a novel composition for parenteral application. More particularly, the present invention relates to an oil composition of dihydropolyprenols for enhancing the immune system of animals.

BACKGROUND OF THE INVENTION

Dihydropolyprenols are a class of known polyprenols that have been found to enhance nonspecific host defenses against a variety of pathogenic microbes in rodents, cows, calves, pigs and swine. Because of their properties of enhancing host resistance, these compounds may be utilized as agents to treat or control infections in animals and human beings.

However, it is becoming increasingly evident that drug development involves much more than merely finding the compound with maximum biological activity. Many other aspects must be considered before a potent active compound can become a medicinal product. Items of high importance are the stability of the active agent, the absorption behavior from the intended site of administration, the physical state of the active agent, and many other related considerations. Economic factors such as the cost of the bulk drug are additional considerations to those of the properties of the active agent itself.

Recognizing these problems, the present invention provides an unexpected oil composition of dihydropolyprenols, which is pharmaceutically elegant and avoids all the problems noted above. This oil composition limits the components to just the vehicle (i.e., oil) and dihydropolyprenols to be efficacious; therefore, it has the potential for a longer shelf-life as there are fewer components interacting with dihydropolyprenols in a detrimental manner. The oil composition also protects dihydropolyprenols from oxidation, a primary degradation pathway for polyprenols, since oxygen would need to diffuse through the oil vehicles to the dihydropolyprenols and more advantageously some oils contain endogenous antioxidants. In addition, physical stability is not a concern with an oil composition since it is a single phase solution. On the other hand, other formulations such as, for example, emulsions disclosed in the related art, are two phases and have the possibility of interreacting each other with time.

The oil composition of the present invention is easy to administer since it can be more concentrated than emulsion formulations, which results in less volume being injected into animals. For example, the emulsion formulation is normally made at 10 mg/mL while our oil based formulation can be at least 150 mg/mL, with a 15-fold reduction in the volume. Also, this oil composition can be easily syringed since the viscosity is low enough for it to flow through a typically used syringe and needle while for example, an implantable pellet containing dihydropolyprenols would be more difficult to administer to animals.

Finally, a simple method is available for manufacturing oil compositions of dihydropolyprenols at a large production size while more complicated and expensive methods are often required for other dosage forms.

INFORMATION DISCLOSURE

U.S. Pat. No. 4,624,966 discloses $\beta,\gamma$-dihydropolyprenyl alcohol derivatives useful as a phylactic agent against human and animal infectious diseases and methods of use them.

U.S. Pat. No. 4,839,389 discloses polyprenyl alcohol containing injections comprising polyprenyl alcohols and lecithin as essential ingredients.

U.S. Pat. No. 5,139,740 discloses a composition for soft capsules containing a polyprenyl compound, a surfactant and/or an unsaturated aliphatic acid.

U.S. Pat. No. 5,280,048 discloses a method of using a polyprenyl compound against infection.

Additional references of general interest include the following:

H. Nagahata, G. J. Kociba, H. Noda, M. Koiwa and M. Kimura, "Effects of Dihydroheptaprenol on the Neutrophil Function of Postpartum Dairy Cows", *Veterinary Immunology and Immunopathology*, 29, pp. 163–169 (1991).

O. Yoneyama, S. Osame, S. Ichijo, M. Kimura, S. Araki, M. Suzuki and E. Imamura, "Effects of Dihydroheptaprenol on Neutrophil Functions in Calves", *British Veterinary Journal*, 145, pp. 531–537 (1989).

O. Yoneyama, S. Osame, M. Kimura, S. Araki and S. Ichijo, "Enhancement of Neutrophil Function by Dihydroheptaprenol in Adult Cows", *Japan Journal of Veterinary Science*, 51(6), pp. 1283–1286 (1989).

T. Watari, R. Goitsuka, H. Koyama, T. Sako, T. Uchino, S. Araki, A. Hasegawa and S. Motoyoshi, "Effect of Dihydroheptaprenol on Nitroblue Tetrazolium Reduction by Swine Alveolar Macrophages", *Japan Journal of Veterinary Science*, 51(3), pp. 630–631 (1989).

S. Araki, M. Suzuki, K. Ogura, M. Kimura, E. Imamura, C. Kuniyasu, K Kagaya and Y. Fukazawa, "Enhancement of Phagocytosis and Bactericidal Activity of Neutrophils in Miniature Pigs by Dihydroheptaprenol, A Synthetic Polyprenol Derivative", *Microbiology, Immunol.*, 33(10), pp. 877–882 (1989).

S. Araki, K. Kagaya, K. Kitoh, M. Kimura and Y. Fukazawa, "Enhancement of Resistance to Escherichia Coli Infection in Mice by Dihydroheptaprenol, a Synthetic Polyprenol Derivative", *Infection and Immunity*, 55(9), pp. 2164–2170 10 (1987).

M. Kimura, S. Araki, T. Nakai and K. Kume, "Protective Effect of Dihydroheptaprenol in Combination with Vaccine to Experimental Actinobacillus Pleuropneumoniae Injection in Guinea Pigs and Pigs", *Japan Journal of Veterinary Science*, 55(4), pp. 627–630 (1993).

E. J. Robb, D. D. Kratzer, C. H.-Ho, and K. J. Dame, "Dose Characterization and Dosage Regime Evaluation of Dihydroheptaprenol in Induced Bovine Pneumonic Pasteurellosis", *Journal of Animal Science*, 71 (Suppl. 1), p. 203 (1993).

SUMMARY OF THE INVENTION

One object of the present invention is to provide a pharmaceutical composition comprising a dihydropolyprenol and an oil vehicle which increase innate resistance to infection and stimulate the immune system of animals and are biologically compatible with the animals.

A further object of the present invention is to provide an oil composition containing a high drug load of a dihydropolyprenol so that a single volume may be used for convenient administration.

A still further object of the present invention is to provide an oil composition possessing physical and chemical stability so that a suitable shelf-life is obtained when the composition is packaged in an economically ready-to-use container.

Another object of the present invention is to provide an oil composition having a low viscosity so that the composition may be easily syringed.

Still another object of the present invention is to provide an oil composition that can be manufactured with a simple method so the final cost of the product is minimized.

The objects of the present invention have been accomplished in that the present invention provides an oil composition for parenteral administration, which consisting essentially of a dihydropolyprenol of formula I and a pharmaceutically acceptable oil, wherein n is an integer of 5 to 7.

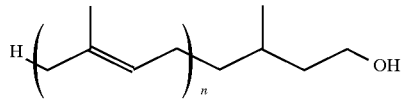

DETAILED DESCRIPTION OF THE INVENTION

Surprisingly and unexpectedly, it has been found that the oil compositions of the present invention which contain essentially no water enhance the utilization of dihydropolyprenols of formula I. They provide a drug deliver vehicles which are stable, easy to administrate and less costly to manufacture.

Dihydropolyprenols are a class of known compounds. Their activities for enhancing the immune system of animals and the methods for preparing them are disclosed in U.S. Pat. No. 4,624,966; U.S. Pat. No. 4,839,389; U.S. Pat. No. 5,139,740; U.S. Pat. No. 5,280,048, which are incorporated herein by reference.

The preferred dihydropolyprenol of formula I to make an oil composition of the present invention is dihydroheptaprenol, a compound of formula I wherein n is 6.

Animals refer to livestock, poultry and companion animals. However, the invention may also be practiced with other vertebrates, and with the lower species comprising the non-vertebrates.

The oil compositions of the present invention may be prepared by combining a dihydropolyprenol of formula I with a pharmaceutically acceptable oil. Methods for making such compositions are conventional techniques and are well-known to those skilled in the art. For example, the required weight or volume of oil is placed into a glass or stainless steel vessel. The oil may be filtered through a sterilizing filter (0.22 micron filter) into the vessel. The weight or volume of a dihydropolyprenol for a stated concentration is calculated and poured into the vessel containing the oil. The two solutions are then stirred until a homogeneous mixture is obtained. The length of stirring time depends on the size of the vessels and the type of mixing devices used. Generally, for a batch size of 100 mL it takes about 5 minutes to obtain a homogeneous solution, and a batch size of 1000 L it may require about 30 minutes.

Once the homogeneous solution is made, it may be filtered through a sterilizing filter (0.22 micron filter) and filled into vials.

The term "pharmaceutically acceptable" refers to those properties which are biologically compatible with the treated subjects from a pharmacological/toxicological point of view and to the manufacturing pharmaceutical chemist from a physical/chemical point of view regarding stability, solubility and bioavailability.

The pharmaceutically acceptable oil is coconut oil.

The terms "Miglyol 810", "Miglyol 812", and "Miglyol 829" refer to different grades of fractionated and purified coconut oil consisting mainly of medium chain triglycerides sold under the trademark Miglyol by Huls, Inc.

The oil compositions of the present invention are provided in a form intended to be administered parenterally. The preferred route of administration in livestock is subcutaneous in order to minimize damage to edible tissue. However, intramuscular or other parenteral routes of administration may also be used.

The quantity of a dihydropolyprenol of formula I to be used and the concentration of an oil composition of the present invention may be varied or adjusted widely depending on the potency of the particular compound used, the required dose, the desired concentration, and/or the particular animal being treated. Generally, the quantity of active component will range between 0.1 to 1000 mg/kg, and the concentration will range between 1 mg/mL to 500 mg/mL. The upper limit of concentration is reached when the oil composition becomes too viscous to syringe. For example, when using dihydroheptaprenol to prevent bovine respiratory disease (BRD) in feedlot calves the dose may be between 1 and 10 mg/kg. Another example, when treating feedlot calves at a dose of 2 mg/kg of dihydroheptaprenol to prevent BRD, a 150 mg/mL concentration solution is preferred. Therefore, one injection of 1.3 mL will provide the required dihydropolyprenol for the average animal treated.

The oil compositions of the present invention will be better understood in connection with the following examples, which are intended as an illustration of and not a limitation upon the scope of the invention. Without further elaboration, it is believed that one skilled in the art can, using the preceding description and the information provided in the example below, practice the present invention to its fullest extent.

EXAMPLE 1

0.341 g of dihydroheptaprenol is placed into a 20 mL glass beaker containing 10.997 g of Miglyol 812. A magnetic stirring bar is added and the solution stirred for 30 minutes. The solution is then placed into 5 mL glass vials, stoppered, capped and labeled. The dihydroheptaprenol concentration is 30.1 mg/g formulation. The formulation is tested in the Systemic Mouse Protection Test with a challenge dose of *Pasteurella haemolytica* at 28.2 $LD_{50}$.

EXAMPLE 2

0.339 g of dihydroheptaprenol is placed into a 20 mL glass beaker containing 10.996 g of Miglyol 812. A magnetic stirring bar is added and the solution stirred for at least 30 minutes. The solution is then placed into 5 mL glass vials, stoppered, capped and labeled. The dihydroheptaprenol concentration is 26.5 mg/mL formulation. The formulation is tested in the Systemic Mouse Protection Test with a challenge dose of *Pasteurella haemolytica* at 12 $LD_{50}$.

EXAMPLE 3

1.886 g of the product of EXAMPLE 2 is diluted with 26.467 g of Miglyol 810 by mixing for 10 minutes the two liquids in a beaker. The dihydroheptaprenol concentration is 9.8 mg/mL. The formulation is tested in the Systemic Mouse Protection Test with a challenge dose of *Pasteurella haemolytica* at 10 $LD_{50}$.

EXAMPLE 4

0.1 g of dihydroheptaprenol is placed into a 20 mL glass vial followed by the addition of 9.9 g of Miglyol 810. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 22 $LD_{50}$.

EXAMPLE 5

0.1 g of dihydroheptaprenol is placed into a 20 mL glass vial followed by the addition of 9.9 g of Miglyol 812. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 22 $LD_{50}$.

EXAMPLE 6

0.1 g of dihydroheptaprenol is placed into a 20 mL glass vial followed by the addition of 9.9 g of Miglyol 829. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 22 $LD_{50}$.

EXAMPLE 7

0.1 g of dihydroheptaprenol is placed into a 20 mL glass vial followed by the addition of 9.9 g of safflower oil. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 22 $LD_{50}$.

EXAMPLE 8

0.1 g of dihydroheptaprenol is placed into a 20 mL glass vial followed by the addition of 9.9 g of sesame oil. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 25 $LD_{50}$.

EXAMPLE 9

0.1 g of dihydroheptaprenol is placed into a 20 mL glass vial followed by the addition of 9.9 g of soybean oil. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 6 $LD_{50}$.

EXAMPLE 10

0.1 g of dihydroheptaprenol is placed into a 20 mL glass vial followed by the addition of 9.9 g of cottonseed oil. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 9 $LD_{50}$.

EXAMPLE 11

0.1 g of dihydroheptaprenol is placed into a 20 mL glass vial followed by the addition of 9.9 g of peanut oil. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 25 $LD_{50}$.

EXAMPLE 12

0.1 g of dihydroheptaprenol is placed into a 20 mL glass vial followed by the addition of 9.9 g of mineral oil. The vial is then vortexed for 1 minute using a Yamato vortexer set at full speed. After setting for 1 hour the vial is vortexed again for 15 seconds. The vial is stoppered, capped and labeled. The dihydroheptaprenol concentration is 10 mg/g of formulation. The formulation is tested in the Systemic Mouse Protection Test with a challenge dose of *Pasteurella haemolytica* at 9 $LD_{50}$.

EXAMPLE 13

The preparation of the formulation is conducted in a laminar flow hood using good aseptic techniques. 9.02 g of dihydroheptaprenol and 47.73 g of Miglyol 810 which has been filtered through a 0.22 micron filter is placed into a sterile 100 mL glass beaker. A magnetic stirring bar is added and the solution stirred for 10 minutes. The solution is then placed into a 50 mL sterile glass vial, stoppered, capped and labeled. The assayed concentration is 142.2 mg/mL. The placebo is prepared by filtering through a 0.22 micron filter approximately 50 ml of Miglyol 810 into a sterile 50 mL glass vial. The vial is stoppered, capped and labeled. The formulation is tested in a *Pasteurella haemolytica* bovine challenge test.

EXAMPLE 14

The preparation of the formulation is conducted in a laminar flow hood using good aseptic techniques. 21.43 g of dihydroheptaprenol and 110.94 g of Miglyol 810 which has been filtered through a 0.22 micron filter is placed into a sterile 200 mL glass beaker. A magnetic stirring bar is added and the solution stirred for 10 minutes. The solution is then placed into 50 mL sterile glass vials, stoppered, capped and labeled. The assayed concentration is 149.8 mg/mL. The placebo is prepared by filtering through a 0.22 micron filter approximately 50 mL of Miglyol 810 into a sterile 50 mL glass vial. The vial was stoppered, capped and labeled. The formulation is tested in a *Pasteurella haemolytica* bovine challenge test.

EXAMPLE 15
Systemic Mouse Protection Test

The compositions of EXAMPLES 1–12 are evaluated in a *Pasteurella haemolytica* mouse systemic protection test. In this test each mouse is given subcutaneously a dose of a composition, then challenged with *P. haemolytica* 24 hours later. The challenge dose in EXAMPLE 1 is 28.2 times as the dose required to kill 50% of the mice ($LD_{50}$ =28.2). The challenge doses of other examples are listed in Table 1. The dose varies from 25 to 400 mg/g. The compositions are diluted with the oil being tested prior to dosing so that injectable volumes for a mouse is available. The group receiving 0 mg/kg is injected with Miglyol 812 as a control. The strain of *P. haemolytica* used is UC6531 and is originally isolated from a case of bovine respiratory disease. The test strain is maintained on 3 mm glass beads immersed in trypticase soy broth (Becton-Dickinson Microbiology Systems) with 10% glycerol and held at −70° C. until revived. The number of mice that survive after seven days are recorded. From the number of survivals, an $ED_{50}$ is calculated. TABLE 1 summaries the results of the test.

EXAMPLE 16

*Pasteurella haemolytica* Bovine Challenge Test

The composition of EXAMPLE 13 is evaluated in a *Pasteurella haemolytica* bovine challenge test. In this test, Holstein bull calves 35 to 50 days old are randomly assigned by weight to treatment groups. Fifteen animals are assigned to a placebo group which received only the Miglyol 810 vehicle or a group receiving 4 mg/kg as the oil formulation. The dose of 4 mg/kg is subcutaneously administered to each animal followed by a challenge 24 hours later. The challenge consisted of intratracheal inoculation of $6\times10^6$ colony forming units (CFU) per calf of virulent *P. haemolytica* (A1) in 10 mL of acidified (pH 4.5) Brain Heart Infusion (BHI) broth followed 4 hours later by a challenge of $4\times10^8$ CFU per calf of *P. haemolytica* in 10 mL of BHI broth without acidification. Calves are observed for 10 days, weighed, euthanized and necropsied. Decision criteria are mortality, the number of calves gaining 2.27 kg during the study and the calculated lung consolidation score. The study is designed to have an 80% power of detecting 21–23% differences in mortality and growth with alpha=0.2.

None of the calves in the group receiving 4 mg/kg died while a significant difference 2 of the 15 calves in the placebo group died (P=0.04, one sided). Significantly, more calves (P=0.006, one sided) gain 2.27 kg in the 4 mg/kg group (14 of 15) compared to the negative control (7 of 15). There is no significant difference in lung lesion scores.

The composition EXAMPLE 14 is evaluated in the same *Pasteurella haemolytica* bovine challenge test used for EXAMPLE 13. Fifteen animals are assigned to a placebo group which received only the Miglyol 810 vehicle, a group receiving 0.5, mg/kg, 1 mg/kg, 2 mg/kg or 4 mg/kg as the oil formulation. The dose of dihydroheptaprenol is subcutaneously delivered to each animal followed by a challenge 24 hours later. Calves are again observed for 10 days, weighed, euthanized and necropsied. Decision criteria are mortality, the number of calves gaining 2.27 kg during the study and the calculated lung consolidation score. The study is designed to have an 80% power of detecting differences.

Mortality is 4 of 15 (placebo), 2 of 15 (0.5 and 1 mg/kg), 0 of 15 (2 mg/kg) and 1/15 (4 mg/kg, with the one animal dying from torsion of the bowel and not related to the challenge). Statistically fewer deaths ($P\leqq0.11$, one sided) are present with those groups receiving 0.5 mg/kg or more of dihydroheptaprenol. The number of calves gaining more than 2.27 kg are 3 of 15 (placebo), 5 of 15 (0.5 mg/kg), 9 of 15 (1 mg/kg), 12 of 15 (2 mg/kg) and 13 of 15 (4 mg/kg). Those treatment groups receiving 1 mg/kg or more of dihydroheptaprenol are statistically different ($P\leqq0.03$, one sided) from the placebo group. The lung lesion scores are 18.9±8.4% (placebo), 22.7±16.8% (0.5 mg/kg), 15.6±14.1% (1 mg/kg), 17.8±19.9% (2 mg/kg) and 9.3±10.2% (4 mg/kg). The lung lesion scores of calves administered 4 mg/kg are significantly lower (P=0.03, one sided) then calves of the placebo group.

TABLE 1

SYSTEMIC MOUSE PROTECTION TEST

| Example No. | $LD_{50}$ | $ED_{50}$ mg/kg |
|---|---|---|
| 1 | 28.2 | 200 |
| 2 | 12 | 50 |
| 3 | 10 | 20 |
| 4 | 22 | 32 |
| 5 | 22 | 32.6 |
| 6 | 22 | 49.8 |
| 7 | 22 | <25 |
| 8 | 25 | <12.5 |
| 9 | 6 | 25.7 |
| 10 | 9 | <25 |
| 11 | 25 | <12.5 |
| 12 | 9 | 79.2 |

We claim:

1. An oil composition for parenteral administration consisting essentially of dihydropolyprenol of formula I and a pharmaceutically acceptable oil

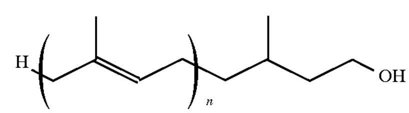

I wherein n is an integer of 5 to 7.

2. A dihydropolyprenol of formula I according to claim 1 wherein n is 6.

3. A dihydropolyprenol of formula I according to claim 1 which is dihydroheptaprenol.

4. An oil composition according to claim 1 wherein said oil is coconut oil, safflower oil, sesame oil, soybean oil, cottonseed oil, peanut oil or mineral oil.

5. An oil according to claim 1 which is coconut oil.

6. An oil according to claim 1 which is Miglyol.

7. An oil according to claim 1 which is peanut oil.

8. An oil according to claim 1 which is sesame oil.

9. An oil according to claim 1 which is safflower oil.

10. An oil composition according to claim 1 wherein a dihydropolyprenol of formula I is present at a concentration about 1 mg/mL to about 500 mg/mL.

* * * * *